US00PP13268P3

(12) United States Plant Patent
Fryer

(10) Patent No.: US PP13,268 P3
(45) Date of Patent: Nov. 26, 2002

(54) SHRUB ROSE PLANT NAMED 'FRYYEOMAN'

(75) Inventor: Gareth Fryer, Knutsford (GB)

(73) Assignee: Weeks Wholsale Rose Grower, Inc., Upland, CA (US)

( * ) Notice: Subject to any disclaimer, the term of this patent is extended or adjusted under 35 U.S.C. 154(b) by 2 days.

(21) Appl. No.: 09/736,894

(22) Filed: Dec. 12, 2000

(65) Prior Publication Data

US 2002/0073449 P1 Jun. 13, 2002

(51) Int. Cl.[7] ..... A01H 5/00
(52) U.S. Cl. ..... Plt./107

(58) Field of Search ..... Plt./107

(56) References Cited

U.S. PATENT DOCUMENTS

PP9,178 P * 6/1995 Ogilvie ..... Plt./107
PP9,324 P * 10/1995 Zary ..... Plt./107

* cited by examiner

*Primary Examiner*—Bruce R. Campell
*Assistant Examiner*—W C Baker
(74) *Attorney, Agent, or Firm*—Christie, Parker & Hale, LLP

(57) ABSTRACT

A new variety of Shrub rose suitable for garden decoration, having large clusters of flowers of pastel pink coloration.

1 Drawing Sheet

BACKGROUND OF THE INVENTION

This invention relates to a new and distinct variety of Shrub Rose. The varietal denomination of the new variety is *Rosa hybrida* cv. 'FRYyeoman'. It has as its seed parent the variety known as 'Amruda' (unpatented) and as its pollen parent the variety known as 'Holfairy' (unpatented).

SUMMARY OF THE INVENTION

Among the features which distinguish the new variety from other presently available and commercial rose cultivars known to the inventor are the following combination of characteristics: its numerous hairs on the peduncle, its large flowers clusters that are often somewhat pendulous, its distinct dark red pigment at the base of the filaments and top of the hypanthium and its very bunched nearly synstylate styles. The plant has a bushy upright to somewhat spilling plant growth habit, suitable for outdoor garden decoration.

Asexual reproduction of the new variety by budding as performed in Kern County and Upland, Calif., shows that the foregoing and other distinguishing characteristics come true to form and are established and transmitted through succeeding propagations. 'FRYyeoman' may be asexually propagated by cuttings, budding and grafting.

COMPARISON WITH PARENTS

The new rose may be distinguished from its seed parent, 'Amruda', by the following combination of characteristics: whereas 'Amruda' bears double flowers (about 28 to 33 petals) of red coloration, 'FRYyeoman' bears pastel pink flowers with significantly lower petalage (about 10 to about 15 petals). The seed parent has a very low compact growth habit and is classified as a Miniature, whereas the new seedling has a larger upright to somewhat spilling habit and is classified as a Shrub.

The new variety may be distinguished from its pollen parent, 'HOLfairy', by the following combination of characteristics: whereas 'FRYyeoman' bears medium small flowers (about 4.4 to 5 cms. in diameter) of pastel pink coloration, 'HOLfairy' bears significantly smaller flowers (about 2.8 to about 3.4 cms. in diameter) of pure white coloration. The pollen parent has a significantly smaller mature plant habit than the new seedling.

BRIEF DESCRIPTION OF ILLUSTRATION

The accompanying photograph illustrates 3 to 4 year old rose plants of the new variety and shows the flowering thereof from bud to full bloom depicted in color as nearly correct as it is possible to make in a color illustration of the character. Throughout this specification, color values are based upon the Colour Chart of The Royal Horticultural Society of London, England, (1995 ed.) except where common terms of color definition are employed.

DESCRIPTION OF THE NEW VARIETY

The following description is of 3 to 4 year old rose plants of the new cultivar grown outdoors in Upland, Calif. in the month of August. Phenotypic expression may vary with environmental, cultural and climatic conditions, as well as differences in conditions of light and soil.

FLOWER

The new variety rarely bears its flowers singly, usually in moderately large clusters with numerous flowers per stem. Flowers are borne in regular moderately rounded to pyramidal clusters on medium to long stems (about 22 to about 46 cms.) that are often somewhat pendulous with the weight of the cluster. Outdoors, the plant blooms very abundantly and nearly continuously during the growing season. The flowers have a very slight tea fragrance.

BUD

The peduncle is about 2 to about 3.5 cms. in length. It is somewhat smooth, with numerous fine hairs and very few stipitate glands. Peduncle color is between 147C and 138B, sometimes lightly suffused especially on the side exposed to sun with between 182B and 182A.

Before the calyx breaks, the bud is about 0.5 to about 0.7 cms. in diameter at the widest point, about 1.2 to about 1.5 cms. in length, and pointed to ovoid in shape with a conspicuous hypanthium. The surface of the bud bears some slender foliaceous appendages, very few stipitate glands and many fine hairs, usually with slender entire foliaceous parts extending beyond the tip of the bud about ¼ or more of its length. Bud color is between 147C and 138B, sometimes lightly suffused with between 182B and 182A.

The inner surface of the sepals is covered with fine wooly tomentum; sepal margins are lined with very few stipitate glands and many hairs.

As the petals open (after the calyx breaks), the bud is about 0.8 to about 1.1 cms. in diameter at the widest point, about 1.3 to about 1.7 cms. in length, and very pointed to ovoid in form. The color of the under and upper surfaces of the newly opened petals is between 38B and 55B. At the point where the petal attaches on the upper surface, there is a moderately large zone of near 7B. At the point where the petal attaches on the under surface, there is a smaller zone of similar coloration.

BLOOM

When fully open, the bloom ranges from about 4.4 to about 5 cms. in diameter. Petalage is semi-double with about 10 to 15 petals and 0 to 3 petaloids arranged regularly. When partially open, the bloom form is moderately cupped to somewhat globular, and the petals are loosely spiraled to cupped. When fully open, the bloom form is more flat to cupped, and the petals are loosely cupped to flat to somewhat undulated with petal edges slightly reflexed outward.

PETALS

The substance of the petals is moderately heavy and of medium thickness, with upper and under surfaces somewhat shiny to satiny. The outer petals are broadly oval to obovate in shape with rounded apices. The inner petals are more narrowly obovate in shape with rounded apices.

NEWLY OPENED FLOWER

The under and upper surface of the outer and inner petals is between 49C and 62C. At the point where the petal attaches on the upper surface, there is a somewhat large zone of near 5C. At the point where the petal attaches on the under surface, there is a smaller zone of similar coloration.

The general tonality of the newly opened flower is between 49C and 62C.

THREE DAY OLD FLOWER

The under and upper surface of the outer and inner petals is between 56D and 65D. At the point where the petal attaches on the under and upper surface, there is a moderately small zone of near 5D.

The general tonality of the three day old flower is between 56D and 65D.

On the spent bloom, the petals drop off cleanly, fading to between 65D and 155A.

In August in Upland, Calif., blooms on the bush growing outdoors generally last about four to five or more days. Cut roses from plants grown outdoors and kept at normal indoor living temperatures generally last about three to four or more days.

MALE REPRODUCTIVE ORGANS

Stamens are average in number (average about 65) and are arranged regularly about the pistils. The filaments are of irregular lengths, most with anthers. Filaments are near 3C in color for most of the length, darkening at the very base and onto the top of the hypanthium to between 46A and 53A on the newly opened flower. On the three day old flower, the dark color at the base of the filaments and on the top of the hypanthium is between 53B and 59B. The anthers all open approximately at the same time. Anther color is between 17B and 16A when immature and near 165B at maturity. Pollen is somewhat sparse and near 13D in color.

FEMALE REPRODUCTIVE ORGANS

Pistils vary in number (average about 40). The styles are somewhat uneven and very bunched to nearly synstylate. Stigma and style color is near 16D. Ovaries are usually all enclosed in the calyx.

Hips have not been noted on this variety when grown in Upland, Calif.

FOLIAGE

The compound leaves are usually comprised of three to seven leaflets and are borne abundantly. The five-leaflet leaves are about 8 to about 11 cms. in length, about 7.5 to about 9 cms. in width at the widest point and matte to very slightly semi-glossy in finish. The terminal leaflets are about 3.8 to about 5.2 cms. in length and about 2.4 to about 3.3 cms. in width at the widest point; oval to slightly ovate in shape with somewhat acute apices and somewhat round to acute bases. Their margins are usually simply serrate.

The upper surface of the mature leaf is between 139B and 137A. The under surface of the mature leaf is between 138B and 191A. The upper surface of the young leaf is between 146A and 146C, sometimes lightly edged with between 183D and 182C. The under surface of the young leaf is of similar coloration but with more suffusion of the darker pigment.

The rachis is somewhat rough. The upper side is moderately grooved with many stipitate glands on the edges of the grooves. The under side of the rachis is moderately smooth with numerous fine hairs. On the young growth, the upper side of the rachis is often moderately suffused with between 183D and 182C.

The stipules are about 0.9 to about 1.3 cms. in length and somewhat narrow width with straight points that usually turn out at an angle of less than 45 degrees and sometimes recurve somewhat down toward the stem.

The plant displays an above average degree of resistance to powdery mildew and rust as compared to other commercial varieties grown under comparable conditions in Upland, Calif.

GROWTH

The plant has a bushy upright to somewhat spilling medium height growth habit (about 110 to about 150 cms. in height and spread at the widest point), with very full branching. It displays very vigorous growth. The sepals are about 5 in number, about 1.7 to about 2.4 cms in length and about 0.4 to about 0.7 cm in width at the widest point. The under surface of the sepal is between 147C and 138B, sometimes lightly suffused with between 182B and 182A. The upper surface of the sepal is between 139C and 148D. The sepals are somewhat lanceolate in shape with a moderately truncate base.

The color of the major stems is between 147C and 138B. They bear very few large prickles that are about 0.5 to about 0.7 cms. in length. The large prickles are almost straight and angled moderately downward with a moderately narrow oval base; prickle color is near 166C. The major stem bears no small prickles.

The color of the branches is between 147B and 139B. They bear very few large prickles that are of similar size and shape to the large prickles on the major stems; prickle color is between 160A and 162B. The branches bear no small prickles.

The color of the new shoots is between 147C and 138A, sometimes lightly suffused with between 182B and 182A. They bear very few large prickles that are of similar size and shape to the large prickles on the major stems; prickle color is near 182C. The shoots bear no small prickles.

I claim:

1. A new and distinct Shrub rose plant of the variety substantially as described and illustrated herein.

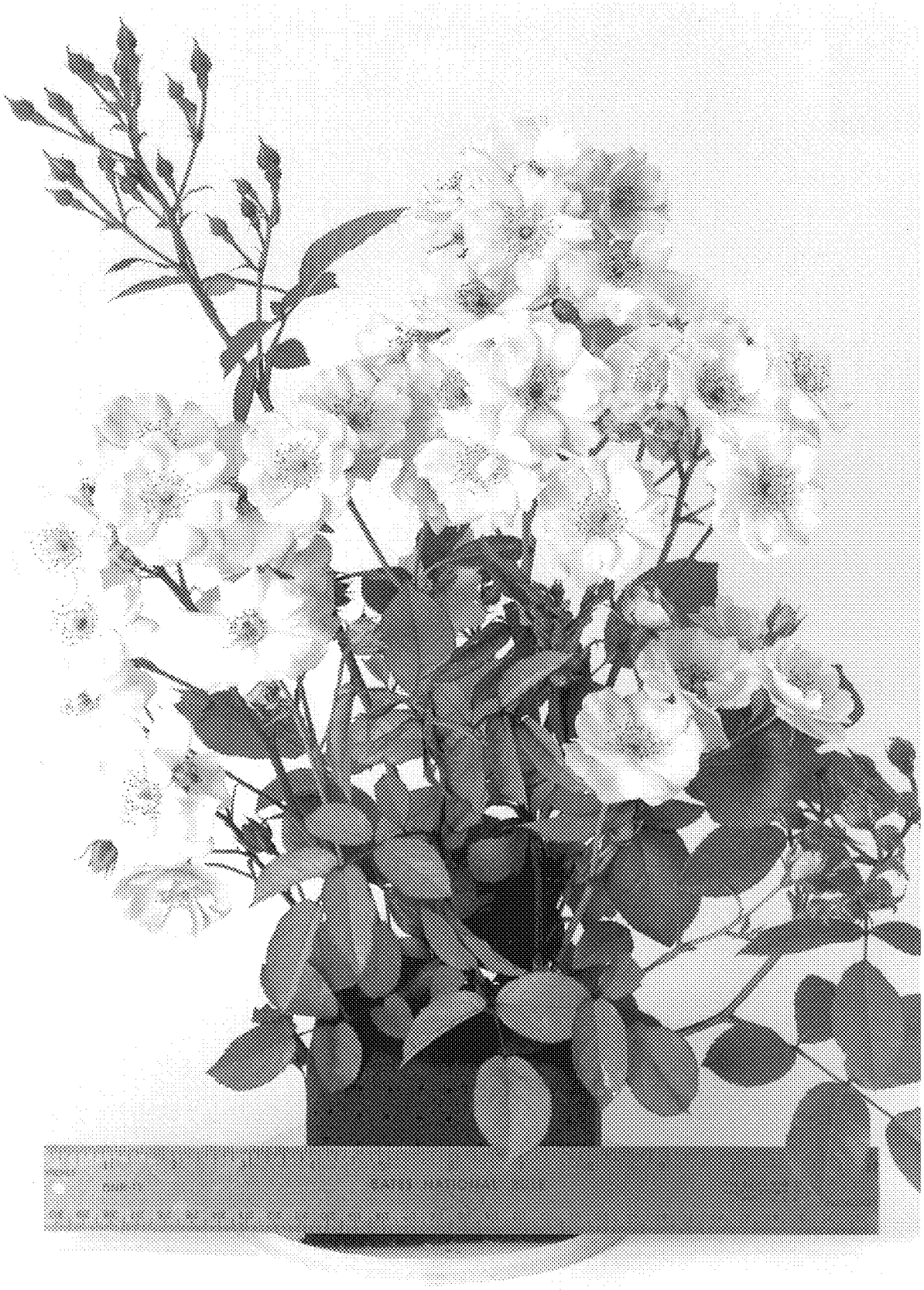

* * * * *